(12) United States Patent
Cutler

(10) Patent No.: US 8,739,794 B2
(45) Date of Patent: Jun. 3, 2014

(54) ORAL DEVICE

(76) Inventor: Harold E. Cutler, Waukegan, IL (US)

(*) Notice: Subject to any disclaimer, the term of this patent is extended or adjusted under 35 U.S.C. 154(b) by 1952 days.

(21) Appl. No.: 10/593,172

(22) PCT Filed: Nov. 4, 2005

(86) PCT No.: PCT/US2005/040029
§ 371 (c)(1),
(2), (4) Date: Sep. 15, 2006

(87) PCT Pub. No.: WO2006/052756
PCT Pub. Date: May 18, 2006

(65) Prior Publication Data
US 2008/0178888 A1    Jul. 31, 2008

Related U.S. Application Data

(60) Provisional application No. 60/522,763, filed on Nov. 4, 2004.

(51) Int. Cl.
*A61M 16/00* (2006.01)
*A62B 9/06* (2006.01)

(52) U.S. Cl.
USPC ..................................... 128/207.14; 128/848

(58) Field of Classification Search
USPC ................. 128/207.14, 200.26, 207.15, 859, 128/201.26, 860, 861, 862, 848
See application file for complete search history.

(56) References Cited

U.S. PATENT DOCUMENTS

| | | | |
|---|---|---|---|
| 1,592,345 A | | 7/1926 | Drager |
| 4,669,459 A | | 6/1987 | Spiewak et al. |
| 5,174,284 A | * | 12/1992 | Jackson ................... 128/200.26 |
| 5,590,643 A | * | 1/1997 | Flam ........................ 128/200.26 |
| 5,626,128 A | | 5/1997 | Bradley et al. |
| 5,915,385 A | * | 6/1999 | Hakimi .......................... 128/848 |
| 5,950,624 A | | 9/1999 | Hart |
| 6,257,238 B1 | * | 7/2001 | Meah ............................. 128/859 |
| 6,517,549 B1 | * | 2/2003 | Dennis .......................... 606/108 |
| 6,675,804 B1 | * | 1/2004 | Pivovarov ..................... 128/848 |
| 2003/0089371 A1 | * | 5/2003 | Robertson et al. ....... 128/201.26 |
| 2004/0211430 A1 | * | 10/2004 | Pivovarov ..................... 128/848 |
| 2006/0207597 A1 | * | 9/2006 | Wright ..................... 128/206.11 |

* cited by examiner

*Primary Examiner* — Justin Yu
*Assistant Examiner* — Colin W Stuart
(74) *Attorney, Agent, or Firm* — Brooks Kushman P.C.

(57) ABSTRACT

An oral device is disclosed. The oral device comprises a mouthpiece member, a tube member and an attachment member. The mouthpiece member comprises a resilient material, and is adapted to fit within the contours of the teeth of a wearer. The tube member is affixed, at a first end, to the mouthpiece member, and extends outward from the mouthpiece member towards the soft palate of the mouth of the wearer. The attachment member is attached to the mouthpiece member at at least one location. Finally, the tube member defines an opening, which prevents the collapse of the soft palate of the wearer by allowing for the free transfer of air between the wearer and the environment.

10 Claims, 5 Drawing Sheets

ORAL DEVICE

FIELD OF THE PRESENT INVENTION

The Present Invention relates to an oral device which is worn by a wearer and, more particularly, an oral device worn by a wearer during sleep for the prevention of various "somno-respiratory" conditions (i.e., conditions that affect the breathing of a sleeping individual), including, for example, sleep apnea, also known as airway occlusion, and/or snoring.

BACKGROUND OF THE PRESENT INVENTION

The phrase "sleep apnea" generally refers to a condition in which a person, who is initially asleep, stops breathing due to airway blockage, usually as a result of the collapsing of the soft palate. Although sometimes known as "airway occlusion," the term "apnea" more accurately refers to the actual cessation of breathing. In chronic states, sleep apnea may tend to lead to various physiologic conditions, including, for example, hypoxema, hypercapnia and congestive heart failure. Although the recommended treatment is a tracheostomy, the procedure, unfortunately, may lead to various post-operative complications in the stoma caused by the tracheostomy, leading to a desire for a more efficient and feasible solution.

Although sleep apnea concerns itself with the cessation of breathing, it is important to note that sufferers usually resume breathing within a few seconds, although periods of as long as sixty seconds are not uncommon in serious cases. Sleep apnea is more common amongst people who snore, are obese, consume alcohol or have anatomical abnormalities of the jaw or soft palate. However, atypical cases do occur, and the condition should not be ruled out unilaterally merely because the patient does not fit the profile.

Generally speaking, there are two primary types of sleep apnea, central sleep apnea and obstructive sleep apnea. Central sleep apnea, the rarer of the two, occurs when a problem in the central nervous system (particularly the areas of the brainstem responsible for respiratory drive) interrupts breathing. Overdoses of opiates, including, for example, heroin and morphine, can, in some cases, kill by inducing a severe central sleep apnea (one reason why such drugs are called "respiratory depressants"). Additionally, central sleep apnea is more common at higher elevations.

The Present Invention, however, is concerned more with obstructive sleep apnea, and, therefore, the use of the phrase "sleep apnea" will heretofore be used to mean obstructive sleep apnea. Generally speaking, sleep apnea is caused by the relaxation of the muscles in a person's airway during sleep. While the vast majority of people successfully maintain a patent (i.e., open) upper airway and breathe normally during sleep, a significant number of individuals are prone to severe narrowing (i.e., occlusion) or collapsing of the pharynx or soft palate, such that breathing is impeded or even completely obstructed. As the brain senses a build-up of carbon dioxide, airway muscles are activated which open the airway, allowing breathing to resume, but, in some cases, such as when the muscles cause snoring or a similar reaction, interrupting the person's deep sleep.

It is this recurrent airway obstruction that gives rise to the sleep apnea syndrome, which is also the most common category of sleep-disordered breathing, with 2% of female and 4% of male subjects meeting the minimal diagnostic criteria for sleep apnea of at least 10 apneic events per hour. An "event" can either be an apnea, characterized by the complete cessation of airflow for at least 10 seconds, or a hypopnea, in which airflow decreases by 50 percent for 10 seconds or decreases by 30 percent if there is an associated decrease in the oxygen saturation or an arousal from sleep. To grade the severity of sleep apnea, the number of events per hour is reported as the Apnea-Hypopnea Index. An Index value of less than 5 is considered normal; 5-15 is mild; 15-30 is moderate and more than 30 events per hour characterizes severe sleep apnea.

In addition to the conditions listed above, recurrent episodes of airway obstruction are associated with asphyxia, hypertension, depression and daytime fatigue, since a transient interruption of the sleep cycle accompanies the restoration of airway patency. Most apnetic individuals are not aware of these events, and are usually informed of the symptoms by their sleep partner. The apneic episodes are thought to account for the clinical sequelae (symptoms that arise from a particular condition), which include increased incidence of chronic hypertension, a 700% rise in road traffic accidents, excessive daytime somnolence (similar, but unrelated to narcolepsy), social and family disruption, and cardiac arrhythmias and morbidity. Obstruction of the upper airway may also be a cause of or may contribute to sudden infant death syndrome.

The management of sleep apnea was revolutionized with the introduction of continuous positive airway pressure, in which the airway of the apnetic is forced open through the use of a positive stream of air pressure into the lungs of the apnetic. One such method is described in U.S. Pat. No. 5,950, 624 to Hart, the contents of which are hereby incorporated herein in their entirety. Hart discloses a rigid oral appliance for installation within the mouth of an individual to prevent obstruction of the natural airway of the individual and to enhance natural ventilation during sleep. Hart also discloses an embodiment in which the oral appliance may be used without an external positive air supply.

However, Hart is deficient in a number of aspects that ultimately prove it disadvantageous to solving the problem of managing sleep apnea. First, Hart describes a mouthpiece member that is rigid in nature and must be molded to the contours and structure of an individual patient. The necessity of requiring dental molds to be taken and a mouthpiece member created by a lab and fitted to the wearer by a physician greatly reduces the effectiveness of treatment on the general population due primarily to excessive cost. Second, the device disclosed in Hart is, by its design, maximally intrusive. It is intended to fill the entire oral cavity of the wearer. As a result, and as with any foreign object which would be inserted into one's oral cavity during sleep, the natural reaction of the body would be to reject or remove the device. Unfortunately, to the extent that the device is in fact removed during sleep, it is totally ineffective. Thus, a design having a relatively small "footprint" is most preferable, as reducing the intrusiveness of the oral cavity would necessarily result in a more comfortable and acceptable situation, increases the acceptance of the device by the wearer, resulting in a decrease in rejection and an increase of effectiveness. Third, the Hart device does not include a retaining strap, which would preferably serve not only to keep the device in place during use, but also to make the device easy to locate and reinsert if it is removed during sleep. Finally, one of the concerns of intra-oral apnea/snoring devices is that insertion of such devices tends to cause salivation in the wearer. Due to its nature, the device disclosed in Hart doesn't seem to facilitate swallowing, since the whole oral cavity is occupied by the device.

Thus, there exists the need for an oral device, used primarily to prevent sleep apnea but also to prevent snoring and the like, which overcomes the disadvantages listed above.

SUMMARY OF THE PRESENT INVENTION

The Present Invention overcomes the deficiencies listed above by providing a flexible, easy to wear device which will prevent instances of sleep apnea from occurring. To this end, an oral device is disclosed.

In one embodiment, the oral device comprises a mouthpiece member, a tube member and an attachment member. The mouthpiece member comprises a resilient material, and is adapted to fit within the contours of the teeth of a wearer. The tube member is affixed, at a first end, to the mouthpiece member, and extends outward from the mouthpiece member towards the soft palate of the mouth of the wearer. The attachment member is attached to the mouthpiece member at at least one location. Finally, the tube member defines an opening, which prevents the collapse of the soft palate of the wearer by allowing for the free transfer of air between the wearer and the environment.

In another embodiment, the oral device comprises a mouthpiece member, a tube member, a palate member and an attachment member. The mouthpiece member comprises a resilient material, and is adapted to fit within the contours of the teeth of a wearer. The tube member is affixed, at a first end, to the mouthpiece member, and extends outward from the mouthpiece member towards the soft palate of the mouth of the wearer. The palate member extends from a second end of the tube member and is curved upwards to maintain contact with the soft palate of the wearer. The second end of the tube member is opposite the first end of the tube member. The attachment member is attached to the mouthpiece member at at least one location. Finally, the tube member defines an opening, which prevents the collapse of the soft palate of the wearer by allowing for the free transfer of air between the wearer and the environment.

In a third embodiment, the oral device comprises a mouthpiece member, a tube member, a palate member, a tongue member and an attachment member. The mouthpiece member comprises a resilient material, and is adapted to fit within the contours of the teeth of a wearer. The tube member is affixed, at a first end, to the mouthpiece member, and extends outward from the mouthpiece member towards the soft palate of the mouth of the wearer. The palate member extends from a second end of the tube member and is curved upwards to maintain contact with the soft palate of the wearer. The second end of the tube member is opposite the first end of the tube member. The tongue member extends from the second end of the tube member and is curved downwards to maintain contact with the tongue of the wearer. The attachment member is attached to the mouthpiece member at at least one location. Finally, the tube member defines an opening, which prevents the collapse of the soft palate of the wearer by allowing for the free transfer of air between the wearer and the environment.

DETAILED DESCRIPTION OF THE PRESENT INVENTION

Figure 1:
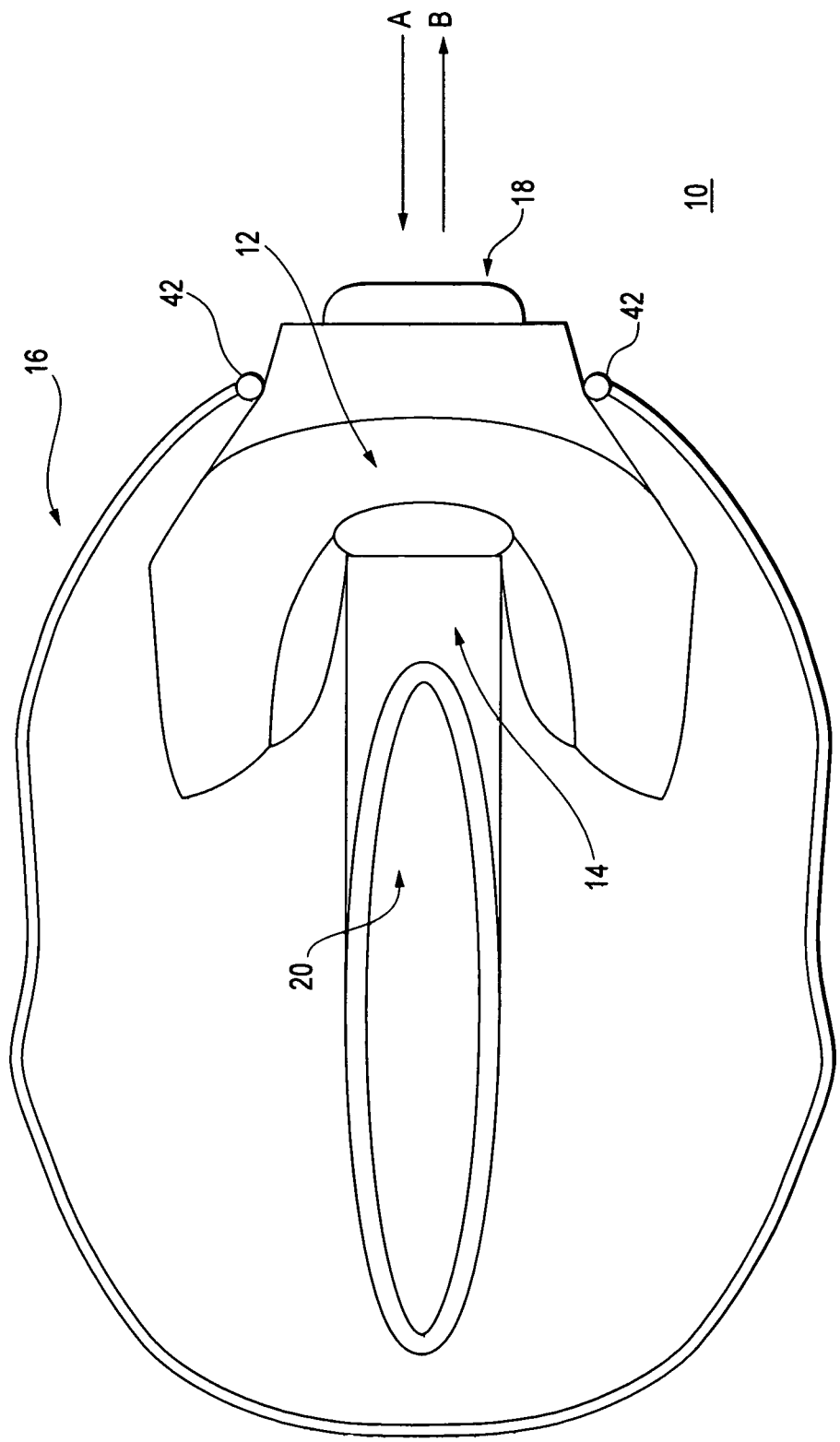
FIG. 1 illustrates a top view of one embodiment of an oral device, constructed in accordance with the teachings of the Present Invention.

Referring to the Figures, in which like numerals refer to like elements, oral device 10, as constructed in accordance with one embodiment of the Present Invention, is illustrated. Referring specifically to FIG. 1, oral device 10 generally comprises mouthpiece member 12, tube member 14 and attachment member 16. Although not illustrated in the Figures, in operation, it is intended that oral device 10 fits within the mouth of a wearer as a treatment for various "somnorespiratory conditions," including, for example, sleep apnea, in which the air passageway in the mouth of the wearer would otherwise become blocked.

Referring again to FIG. 1, mouthpiece member 12 of oral device 10 preferably comprises any member which can be temporarily affixed to, or inserted into, the mouth of the wearer. As illustrated in FIG. 1, mouthpiece member 12 may take the form of, essentially, a scuba-style mouthpiece. It is important to note that this scuba-style mouthpiece is but one possible variation of mouthpiece member 12. Alternatively, mouthpiece member 12 may comprise any of a currently-known mouthpiece in the public domain, including, for example, sports mouthpieces, medical mouthpieces, etc.

However, like the various characteristics of the mouthpieces mentioned above, it is preferred that mouthpiece member 12 be of a resilient material, including, for example, rubber. Alternatively, any other material is, contemplated, including, for example, silicone, vinyl, etc. Any material used should preferably be non-corrosive, because, in use, mouthpiece member 12, as described above, is intended to be temporarily affixed or inserted, such as by gravity or other means, to the mouth of the wearer. Further, mouthpiece member 12 should not be made of a material that would erode the enamel coating of the wearer's teeth, nor should it be made of any material that would cause any harm to the wearer's health. Additionally, mouthpiece member 12 should comprise a flexible and/or resilient material. Again for purposes of health and safety, this characteristic is necessary because, as the wearer wears oral device 10, the wearer's teeth may extend into mouthpiece member 12. Further, it is also preferred that mouthpiece member 12 be made of a non-porous material. During wear, mouthpiece member 12 is in constant contact with the saliva present in the mouth of the wearer. To protect the integrity of mouthpiece member 12, and, actually, of all of oral device 10, it is therefore preferable that the material which comprises mouthpiece member 12 of oral device 10 be of a non-porous material. Finally, it is contemplated that mouthpiece member 12 be made of varying sizes, so as to ensure a proper fit by the wearer, based on the size, age and sex.

To ensure a proper and securing fit, when mouthpiece member 12 is temporarily affixed to, or inserted into, the mouth of the wearer, it is further preferred that mouthpiece member 12 be adapted to fit particularly to the teeth of the wearer. In this manner, not only will mouthpiece member 12 fit comfortably within the mouth of the wearer, but mouthpiece member 12 will be securely fit within the mouth of the wearer, thus allowing for optimum operation of oral device 10. The process of adapting mouthpiece member 12 to fit particularly to the teeth of the wearer may preferably be by any currently-known means, including, for example, subjecting mouthpiece member 12 to heat until it becomes pliable and then conforming, through pressure, the pliable mouthpiece member 12 to the teeth of the wearer.

Mouthpiece member 12 is preferably shaped to define opening 18. Preferably, opening 18 allows for the transfer of air from outside the mouth of the wearer of oral device 10 into the body of the wearer, and vice versa. The transfer of air is illustrated by Arrows A and B; Arrow A indicating the transfer or air from the outside of the mouth of the wearer into the body of the wearer; while Arrow B represents the opposing direction. As illustrated by FIG. 1, tube member 14 is attached to mouthpiece member 12 in such a manner as to extend opening 18 of mouthpiece member 12 into the mouth of the wearer. That is, tube member 14 is attached to mouthpiece member 12 such that air, from the outside of the mouth of the wearer, passes through opening 18 of mouthpiece member 12 and enters inside portion 20 of tube member 14.

As described above, tube member 14 is intended to provide a contiguous and open airway from the mouth of the wearer of oral device 10 through to the throat. This purpose is realized by first allowing air to enter the mouth of the wearer through opening 18 of mouthpiece member 12 and through inside portion 20 of tube member 14. Secondly, this purpose is realized by the ability of tube member 14 to force the soft palate of the wearer to remain open during sleep (the collapsing of which, as described above, is symptomatic of sleep apnea).

Preferably, tube member 14 is comprised of a material sufficient in strength to maintain the openness of the wearer's soft palate, while also maintaining a sufficient degree of light weight so as to not burden the wearer. Additionally, similar to mouthpiece member 12, tube member 14 should also realize the characteristics of mouthpiece portion 12; that being a non-corrosive, non-porous, non-eroding, flexible and resilient material. One preferred material is vinyl, although various other materials, including, for example, polyethylene, rubber, plastic, etc. are contemplated.

Although not required, it is contemplated that tube member 14 be adjustable. In this manner, tube member 14 can be adjusted to fit any size throat, whether the size is long or short, and, conversely, tube member 14 may be adjusted to provide a proper fit against the soft palate of the wearer. The means for adjusting tube member 14 may be by any currently-known means of adjustment, including, for example, via threading means, via a snap-fit arrangement, etc.

Figure 2:
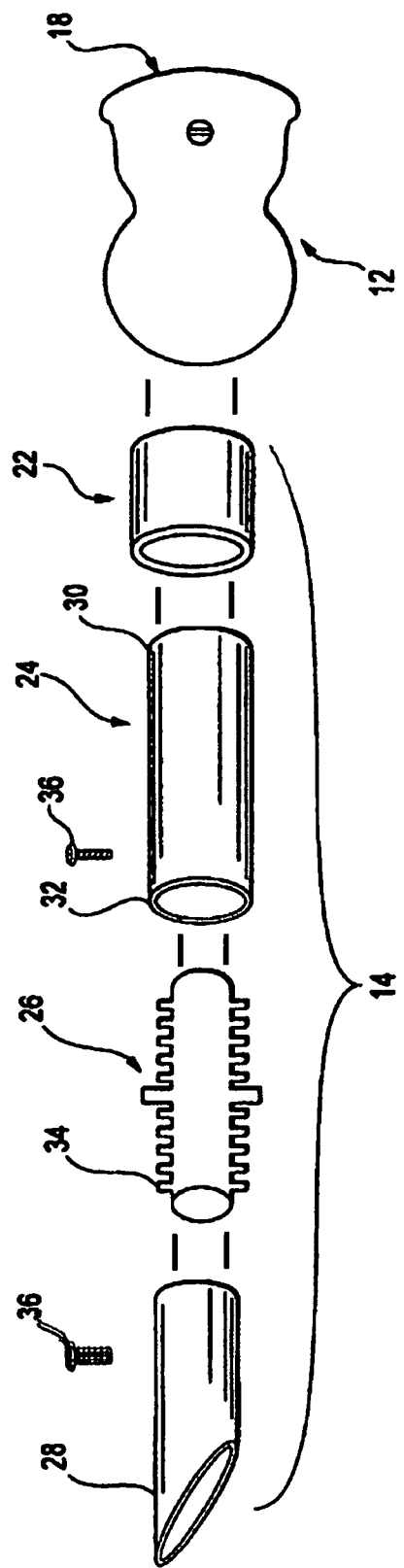
FIG. 2 illustrates one embodiment of a perspective view of the mouthpiece and tube members of the oral device illustrated in FIG. 1.

FIG. 2 illustrates one embodiment for adjusting tube member 14. Referring to FIG. B, tube member 14 is illustrated as comprising securing member 22, first adjustable member 24, adjusting member 26 and second adjustable member 28. Securing member 22, as illustrated, acts as the interface between mouthpiece member 12 and the adjustable aspect of tube member 14. It is intended that securing member 22 fits directly adjacent to opening 18 of mouthpiece member 14. First adjustable member 24 preferably comprises a tube-like shape that fits within or around securing member 22 at one end 30 of first adjustable member 24. At the other end 32 of first adjustable member 24 is disposed adjusting member 26, which bridges the interface between first adjustable member 24 and second adjustable member 28. It is adjusting member 26 that is positioned in such a manner so as to compensate for a longer or shorter throat. More specifically, adjusting member 26 preferably possesses a plurality of ridges 34, upon which first adjustable member 24 and second adjustable member 28 are affixed. Each of the plurality of ridges 34, when in use, serves to maintain the positioning of first adjustable member 24 and second adjustable member 28 vis-à-vis adjusting member 26.

It is further contemplated that a plurality of securing devices 36, shown in FIG. 2 as screws, are used to maintain the proper desired length of tube member 14. Therefore, during use, a wearer may adjust tube member 14 to a desired length by extending or contracting first adjustable member 24 add second adjustable member 28. Upon reaching the desired length, the wearer then uses securing devices 36 to maintain the desired length of tube member 14.

Figure 3:
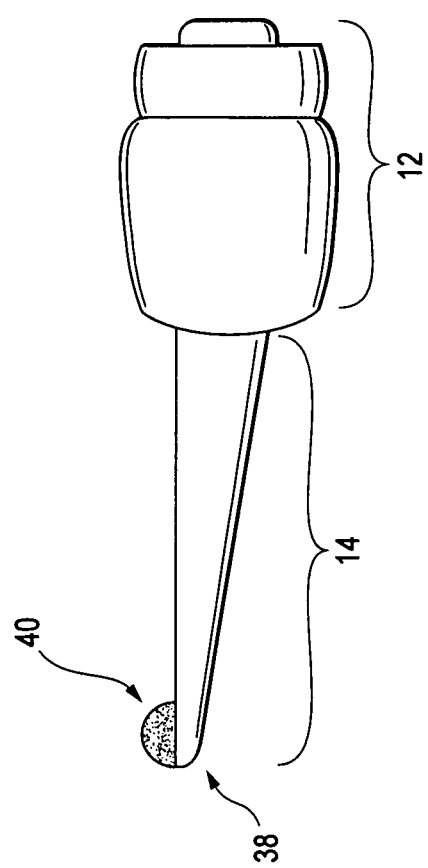
FIG. 3 illustrates a side view of the embodiment of the oral device illustrated in FIG. 1.
Figure 4:
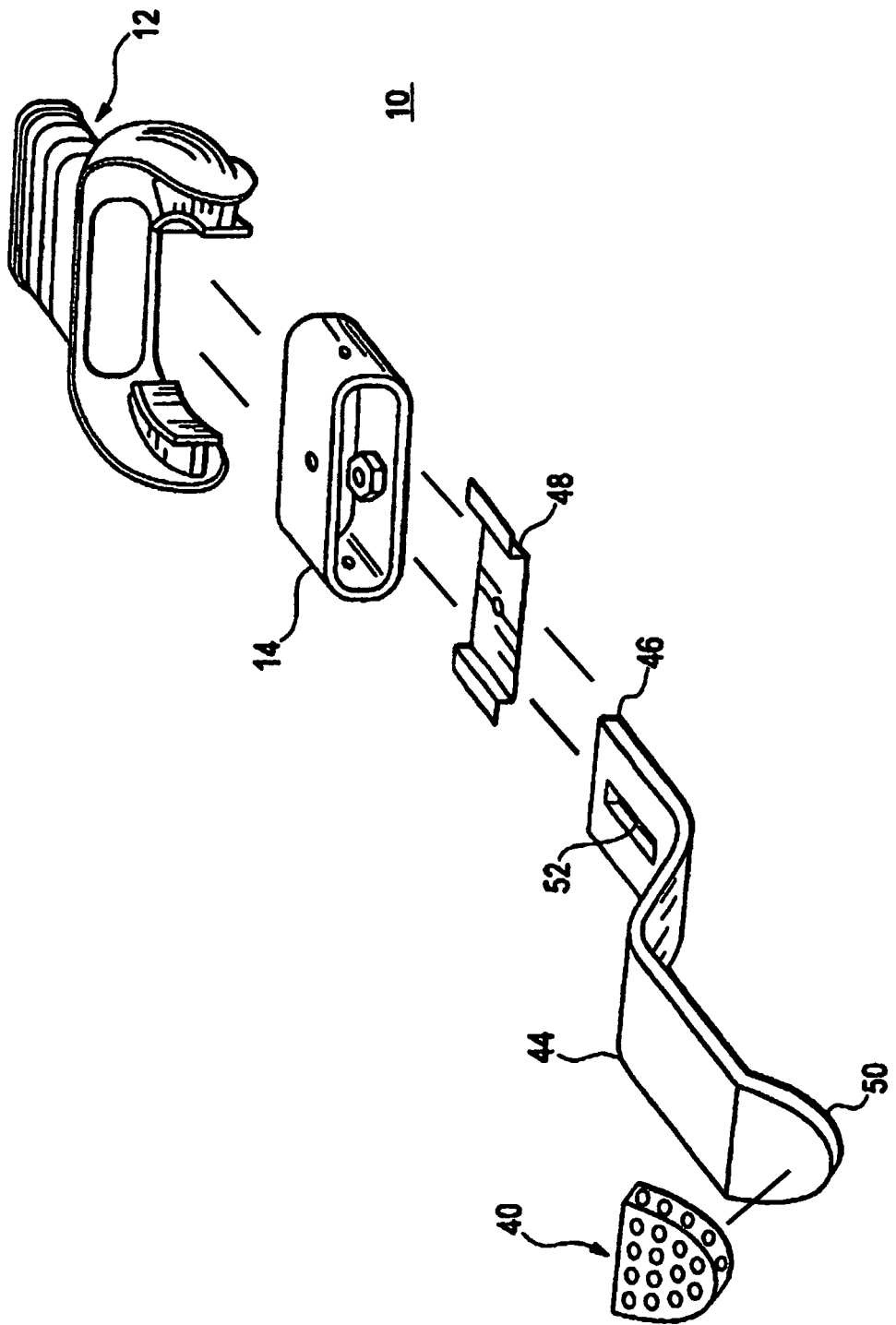
FIG. 4 illustrates a perspective view of a second embodiment of an oral device, constructed in accordance with the teachings of the Present Invention.

In a second embodiment, as illustrated in FIG. 4, it is contemplated that the length of tube member 14 can be drastically reduced, as shown. In such an embodiment, in order to prevent the soft palate of the wearer from collapsing, palate member 44 is attached to tube member 14, and extends posteriorly therefrom. In this embodiment, palate member 44 is attached to tube member 14 at one end 46 (preferably via attachment plate 48). As palate member 44 extends to opposing end 50, palate member 44 extends upward into the soft palate of the wearer. This upward extension is accurately shown in FIG. 4, where palate member 44 is shown as curving towards what would be the soft palate of a wearer. The opposing end 50 of the palate member 44 has a downward extending portion. The embodiment of oral device 10 shown in FIG. 4 maintains the advantage, in light of the drastically reduced length of tube member 14, of being not as intrusive as the embodiment of oral device 10 shown in FIGS. 1 and 3.

Additionally, since tube member 14 does not extend posteriorly past the teeth of the wearer, air is drawn into and dispersed throughout the entire oral cavity, as would be the case in normal breathing. Besides adding the comfort of a more natural breathing process, this eliminates the occurrence of drying and scratchiness of the tissue in the retroglossal area.

Preferably, palate member 44 is made of a flexible, non-corrosive, non-porous material, such as, for example, plastic, rubber, coated aluminum, etc., and is of sufficient length and shape for opposing end 50 to reside under the soft palate of the wearer. It is contemplated that palate member 44 may be bent into shape for a particular wearer. Palate member 44 may also include anchoring mechanism 52, which is represented as a slot disposed within palate member 44. A retainer, such as, for example, a screw (not shown), may be inserted through attachment plate 48 and anchoring mechanism 52 to secure the positioning of palate member 44. In this embodiment, palate member 44 provides a platform on which the palate of the user can rest when it collapses as the wearer sleeps, thus ensuring greater patency of the airway. Thus, for this purpose, palate member 44 should also be sturdy enough to withstand any forces exerted upon it by the soft palate. The process of preventing collapse of the soft palate by ensuring the patency of the airway in this manner also prevents the soft palate from vibrating, which alleviates snoring. Similar to the first embodiment, the second embodiment also includes cushion member 40, preferably affixed to end 50 of palate member 44 to prevent any irritation which may occur from the hardness of the material of palate member 14 as it maintains contact against the soft palate of the wearer.

Figure 5:
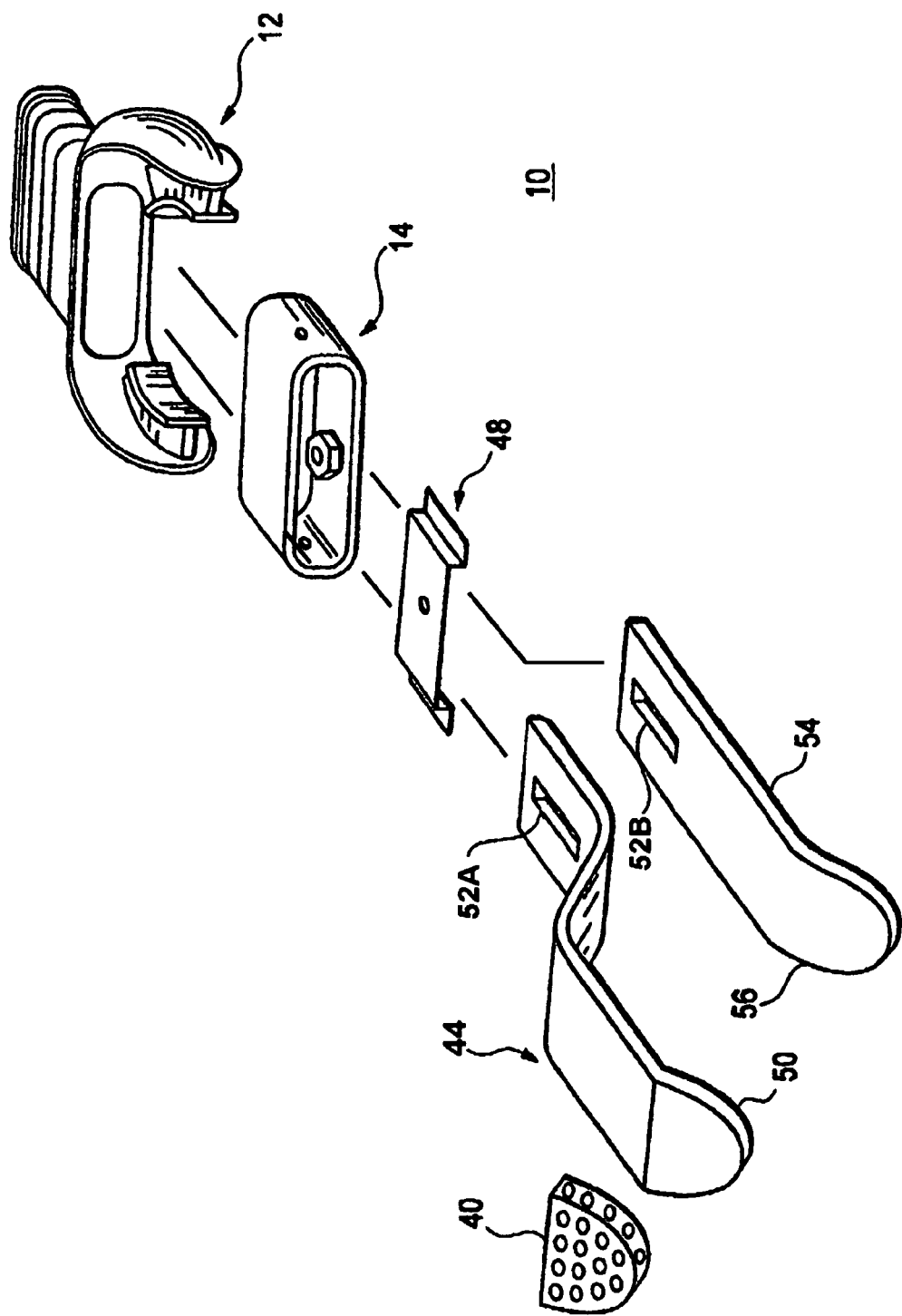
FIG. 5 illustrates a perspective view of a third embodiment of an oral device, constructed in accordance with the teachings of the Present Invention.

A third embodiment of oral device 10 is illustrated in FIG. 5. In the third embodiment, which closely resembles the second embodiment described above, tongue member 54 extends from tube member 14. Tongue member 54 is preferably made of the same material (and possesses the same characteristics) as palate member 44, and is of sufficient length to reach the rear area of the tongue of the wearer. Anterior end 56 of tongue member 54 is curved downward to follow the shape of the back of the tongue. In this embodiment, palate member 44 then provides a platform on which the palate of the user can rest when it collapses as the wearer sleeps, and tongue member 54 holds the tongue of the user down and out of the way, thus ensuring an even greater patency of the airway. The process of preventing collapse of the soft palate by ensuring the patency of the airway in this manner also prevents the soft palate from vibrating, which alleviates snoring. The tongue member 54 may also include anchoring mechanism 52, which is represented as a slot disposed within tongue member 54. A retainer, such as, for example, a screw (not shown), may be inserted through attachment plate 48 and anchoring mechanism 52 to secure the positioning of tongue member 54. Finally, also similar to the first and second embodiments, the third embodiment also includes cushion member 40, preferably affixed to end 50 of palate member 44 to prevent any irritation which may occur from the hardness of the material of palate member 14 as it maintains contact against the soft palate of the wearer.

While only those embodiments set forth above have been described in detail, other configurations and embodiments for the Present Invention exist that are within the spirit and scope of the Present Invention.

What is claimed is:

1. An oral device for a wearer comprising:
   a mouthpiece member, the mouthpiece member being of a resilient material and compliant to contours of the teeth of the wearer;
   a tube member affixed to the mouthpiece member and extending rearward towards the oral cavity of the wearer, the tube member having a first, anterior end and a second, posterior end; and
   a palate member adapted to be adjustably affixed to the tube member and extending from the posterior end of the tube member and having an upwardly inclined portion and ending with a downward extending portion, the palate member being adjusted in position to cause the downward extending portion to maintain contact with the soft palate of the wearer; and
   whereby the tube member defines an opening which allows for free transfer of air between the oral cavity of the wearer and the environment.

2. The oral device of claim 1, further comprising an attachment member attached to the mouthpiece in at least one location and operable to secure the oral device within the oral cavity of the wearer.

3. An oral device for a wearer comprising:
   a mouthpiece member, the mouthpiece member being of a resilient material and compliant to contours of the teeth of the wearer;
   a tube member, the tube member having a first, anterior end and a second, posterior end and being affixed to the mouthpiece member and extending rearward towards the oral cavity of the wearer;
   a soft palate member adjustably affixed to the tube member and having a first (anterior) and second (posterior) end, the first end of the soft palate member extending rearward from the second end of the tube member and having an upwardly inclined portion and the second end of the soft palate member ending with a downward extending portion, the soft palate member being adjusted in position to ensure the downward extending portion maintains upward pressure against the soft palate of the wearer; and
   a tongue member adjustably affixed to the tube member and extending rearward from the second end of the tube member and ending in a portion that is angled downward and extends downward to follow the shape of the back of the tongue, the tongue member being adjusted in position to maintain downward pressure against the tongue of the wearer and reach a rear area of the tongue, the soft palate member and tongue member being adjustable in position independent of each other;
   whereby the tube member defines an opening, the opening allowing for free transfer of air between the oral cavity of the wearer and the environment.

4. The oral device of claim 3, further comprising an attachment member attached to the mouthpiece member in at least one location and operable to secure the oral device within the oral cavity of the wearer.

5. The oral device of claim 4 wherein the attachment member is comprised of a resilient material.

6. The oral device of claim 3 wherein the tongue member is adapted to extend from the second end of the tube member rearward past the teeth of the wearer along the top of the tongue of the wearer.

7. The oral device of claim 3, wherein the tongue member is configured to inhibit rearward movement of the tongue.

8. An oral device for a wearer comprising:
   a mouthpiece member, the mouthpiece member being of a resilient material and compliant to contours of the teeth of the wearer;
   a tube member having a first, anterior end and a second, posterior end, the tube member being affixed to the mouthpiece member and extending rearward towards the oral cavity of the wearer;
   a soft palate member adjustably affixed to the tube member and having a first, anterior end and a second, posterior end, the first end of the soft palate member extending rearward from the second end of the tube member and having an upwardly inclined portion and the second end of the soft palate member ending in a downward extending portion, the soft palate member having a slot disposed therein for adjusting a position of the soft palate member in cooperation with a screw to be received by the tube member, the soft palate member being adjusted in position to cause the downward extending portion to maintain upward pressure against the soft palate of the wearer; and
   a tongue member adjustably affixed to the tube member and extending rearward from the second end of the tube member a length sufficient to reach a rear area of the tongue and ending in a portion that is angled downward and extends downward to follow the shape of the back of the tongue, the tongue member having a slot disposed therein for adjusting a position of the tongue member in cooperation with a screw to be received by the tube member to cause the tongue member to maintain downward pressure against the tongue of the wearer, the positions of the soft palate member and tongue member being adjustable independent of each other;
   whereby the tube member defines an opening, the opening allowing for free transfer of air between the oral cavity of the wearer and the environment.

9. The oral device of claim 8, wherein the soft palate member further comprises a substantially horizontal portion between the upwardly inclined portion and the downward extending portion.

10. The oral device of claim 8, further comprising an attachment member attached to the mouthpiece member in at least one location and operable to secure the oral device within the oral cavity of the wearer.

* * * * *